United States Patent [19]
Griffith et al.

[11] Patent Number: 5,663,364
[45] Date of Patent: *Sep. 2, 1997

[54] HEME BINDING COMPOUNDS AND USE THEREOF

[75] Inventors: Owen W. Griffith, Milwaukee; Krishnaswamy Narayanan, Wauwatosa, both of Wis.

[73] Assignee: The Medical College of Wisconsin Research Foundation, Inc., Milwaukee, Wis.

[*] Notice: The term of this patent shall not extend beyond the expiration date of Pat. No. 5,464,858.

[21] Appl. No.: 550,645

[22] Filed: Oct. 31, 1995

Related U.S. Application Data

[63] Continuation of Ser. No. 354,257, Dec. 12, 1994, Pat. No. 5,464,858, which is a continuation of Ser. No. 87,371, Jul. 7, 1993, Pat. No. 5,424,447.

[51] Int. Cl.$^6$ .................. C07D 233/64; C07D 207/335
[52] U.S. Cl. ...................... 548/335.5; 548/336.1; 548/340.1; 548/562
[58] Field of Search .................. 548/335.5, 336.1, 548/340.1, 562; 562/433, 439, 440, 560, 561, 562; 514/565

[56] References Cited

U.S. PATENT DOCUMENTS

| | | | |
|---|---|---|---|
| 380,945 | 1/1888 | Murad et al. | 564/227 |
| 3,637,837 | 1/1972 | Fujimoto et al. | 562/556 |
| 3,798,269 | 3/1974 | Cutler et al. | 564/59 |
| 4,001,267 | 1/1977 | Argoudelis | 548/339.1 |
| 4,053,651 | 10/1977 | Ondetti et al. | 548/336.1 |
| 4,438,204 | 3/1984 | Deeg et al. | 436/67 |
| 4,568,640 | 2/1986 | Rubin | 435/70 |
| 4,698,442 | 10/1987 | Nestor et al. | 562/560 |
| 5,010,095 | 4/1991 | Sterk et al. | 548/335.5 |
| 5,028,627 | 7/1991 | Kilbourn | 514/565 |
| 5,059,624 | 10/1991 | Monache et al. | 514/616 |
| 5,059,712 | 10/1991 | Griffith | 562/560 |
| 5,115,110 | 5/1992 | Wu et al. | 530/385 |
| 5,133,866 | 7/1992 | Kauvar | 210/635 |
| 5,158,883 | 10/1992 | Griffith | 435/240.2 |
| 5,196,195 | 3/1993 | Griffith | 424/946 |
| 5,216,025 | 6/1993 | Gross et al. | 514/565 |
| 5,246,971 | 9/1993 | Williamson et al. | 514/634 |
| 5,266,594 | 11/1993 | Dawson et al. | 514/560 |
| 5,281,627 | 1/1994 | Griffith | 514/565 |
| 5,286,739 | 2/1994 | Kilbourn et al. | 514/400 |
| 5,296,466 | 3/1994 | Kilbourn et al. | 514/6 |

FOREIGN PATENT DOCUMENTS

| | | |
|---|---|---|
| 175180 | 3/1986 | European Pat. Off. . |
| 1096894 | 1/1961 | Germany . |
| 1804894 | 8/1969 | Germany . |
| 93/13055 | 7/1993 | WIPO . |
| 94/02453 | 2/1994 | WIPO . |

OTHER PUBLICATIONS

Bodanszky, M., et al, The Practice of Peptide Synthesis, Springer–Verlang, New York, 1984, pp. 48, 49, 153, 154.

Feldman, P.L., Tetrahedron Lett., 32, 875–878, 1991.

Rees, D.D., et al, Br. J. Pharmacol., 96, 418–424 (1989).

Gray, G. A., et al, Br. J. Pharmacol., 103, 1218–1224 (May 1991).

Aisaka, K., et al, Biochem. Biophys Res. Commun. 163, No. 2, 710–717 (Sep. 15, 1989).

Julou–Schaeffer, G., et al, Am. J. Physiol. 259, H1038–H1043, Oct. 1990.

(List continued on next page.)

*Primary Examiner*—Richard L. Raymond
*Assistant Examiner*—Deborah Lambkin

[57] ABSTRACT

Inhibitors of nitric oxide formation from arginine useful for treating hypotension, inflammation, stroke and to restore vascular contractile sensitivity to the effects of $\alpha_1$ adrenergic agonists are physiologically active compounds including $N^\delta$-substituted ornithine or $N^\epsilon$-substituted lysine moieties or monoalkyl carbon-substituted $N^\delta$-substituted ornithine or $N^\epsilon$-substituted lysine moieties, having the formula

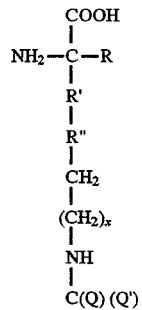

wherein R is $(CH_2)_yCH_3$ or H, R' is $CH_2$ or $C(H)(CH_2)_yCH_3$, and R" is $CH_2$ or $C(H)(CH_2)_yCH_3$, with y ranging from 0 to 5, and x is 0 or 1 and wherein none or only one of R, R' and R" provides an alkyl substituent on ornithine or lysine moiety, and wherein Q is a heme binding moiety and/or a sulfur-containing binding moiety and Q' is $-NH_2$ when there is a double bond between the omega carbon and Q and Q' is $=NH$ when there is a single bond between the omega carbon and Q, and physiologically acceptable acid addition salts thereof.

2 Claims, 5 Drawing Sheets

OTHER PUBLICATIONS

Adnot, S., et al, Proc. Intl. Meeting 1991, Chemical Abstracts 119(5): 46606f.

Hishikawa, K., et al, 1992, Chemical Abstracts 117(1): 5022c.

Ortiz de Montellano, P.R., et al, Cytochrome P–450, Structure, Mechanism and Biochemistry, 273–275, Plenum Press, NY, 1986.

Ialanti, A., et al, European Journal of Pharmacology, 211, 177–182 (1992).

Mulligan, M. S., et al, Proc. Natl. Acad. Sci. U.S.A., 88, 6338–6342, Jul. 1991.

Mulligan, M. S., et al, Br. J. Pharmacol., 107, 1159–1162 (1992).

Misko, T. P., et al, European J. Pharmacol. 223, 119–125 (1939).

Lukic, M. L., et al, Biochem. Biophys. Res. Commun. 153, 1251–1256, 1988.

Miller, M. J. S., et al, Agents Actions 39, Special Conference Issue, C180–C182, 1993.

Corbett, J. A., et al, J. Clin. Invest. 90, 2384–2391, 1992.

Kroncke, K–D, et al, Biochem. Biophys. Res. Commun. 175, 752–758, Mar. 1991.

Corbett, J. A., et al, Proc. Natl. Acad. Sci. U.S.A., 90, 1731–1735, Mar. 1993.

HEME BINDING COMPOUNDS AND USE THEREOF

This is a continuation of application Ser. No. 08/354,257 filed on Dec. 12, 1994, now U.S. Pat. No. 5,464,858, which is a continuation of Ser. No. 08/087,371, filed on Jul. 7, 1993, now U.S. Pat. No. 5,424,447.

TECHNICAL FIELD

The invention is directed to novel inhibitors of biological nitric oxide formation.

BACKGROUND OF THE INVENTION

For several decades nitroglycerin has been administered to humans as a vasodilating agent in the treatment of cardiovascular disease. It has been shown that nitroglycerin so administered is converted in the body to nitric oxide which is the pharmacologically active metabolite. Recently, nitric oxide has been shown to be formed enzymatically as a normal metabolite from arginine in vascular endothelium to provide an important component of endothelium-derived relaxing factors (EDRFs) which are currently being intensively studied as participating in regulation of blood flow and vascular resistance. Macrophages have also been shown to produce nitric oxide in the body as a component of their cell killing and/or cytostatic function.

More recently it has been established that the enzyme forming nitric oxide from arginine, i.e., nitric oxide synthase, occurs in at least two distinct forms, namely a constitutive form and an inducible form. The constitutive form is present in normal endothelial cells, neurons and some other tissues. Formation of nitric oxide by the constitutive form in endothelial cells is thought to play a role in normal blood pressure regulation. The inducible form of nitric oxide synthase has been found to be present in activated macrophages and is induced in endothelial cells and vascular smooth muscle cells, for example, by various cytokines and/or microbial products. It is thought that in sepsis or cytokine-induced shock, overproduction of nitric oxide by the inducible form of nitric oxide synthase plays an important role in the observed life-threatening hypotension. Furthermore, it is thought that overproduction of nitric oxide by the inducible form of nitric oxide synthase is a basis for insensitivity to clinically used pressor agents such as $\alpha_1$ adrenergic agonists in the treatment of septic or cytokine-induced shock patients. Moreover, it is thought that overproduction of nitric oxide by inducible form of nitric oxide synthase is involved in inflammation incident to an immune response.

SUMMARY OF THE INVENTION

It is an object of one embodiment of the invention herein to provide novel arginine or citrulline antagonists which inhibit constitutive form of nitric oxide synthase or inducible form of nitric oxide synthase or both by a binding preferably involving binding to heme cofactor of nitric oxide synthase (i.e., the catalytically important heme cofactor enfolded in a nitric oxide synthase molecule) as a result of including a heme binding moiety.

The novel compounds herein are physiologically active compounds including $N^\delta$-substituted ornithine or $N^\epsilon$-substituted lysine moieties or monoalkyl carbon-substituted $N^\delta$-substituted ornithine or $N^\epsilon$-substituted lysine moieties, having the formula wherein R is $(CH_2)_y CH_3$ or H, R' is $CH_2$ or $C(H)(CH_2)_y CH_3$, and R" is $CH_2$ or $C(H)(CH_2)_y CH_3$, with y ranging from 0 to 5, and x is 0 or 1 and wherein none or only one of R, R' and R" provides an alkyl substituent on ornithine or lysine moiety, and wherein Q is a heme binding moiety and/or a sulfur-containing binding moiety, and Q' is $—NH_2$ when there is a double bond between the omega carbon and Q, and Q' is $=NH$ when there is a single bond between the omega carbon and Q and physiologically acceptable acid addition salts thereof.

Preferably, the moiety Q contains a thiono, sulfide or sulfhydryl sulfur atom.

Preferred compounds are L-thiocitrulline, L-homothiocitrulline, $N^\delta$-(2-thienyl)methylimino-L-ornithine, and $N^\epsilon$-(2-thienyl)methyl-L-lysine.

For compounds where Q' is $=NH$, physiologically acceptable acid addition salts are, e.g., acetate, hydrochloride, sulfate, phosphate, succinate, citrate and propionate.

The term "physiologically active" refers to L-enantiomer whether pure or in admixture with D-enantiomer. The D-enantiomers are not physiologically active. Thus, in the D,L-compounds only the L-enantiomer portion is physiologically active.

Preferably the compounds are pharmaceutically pure, i.e., more than 99% by weight pure (on a water free basis) and contain from 99% to 100% by weight of L-enantiomer (on an L- and D-enantiomer basis).

It is an object of another embodiment herein to provide methods for prophylaxis or treatment of a subject for systemic hypotension or expected systemic hypotension caused by pathological overproduction of nitric oxide from arginine by nitric oxide synthase induced in vascular smooth muscle or endothelial cells in said subject by a cytokine or by a bacterial endotoxin. One of these methods comprises administering to said subject of a therapeutically effective amount of a compound of the invention herein. Another of these methods comprises administering to said subject a conventional amount of at least one $\alpha_1$ adrenergic agonist and an amount of compound of the invention herein effective to restore vascular contractile sensitivity to the effects of said $\alpha_1$ adrenergic agonist.

It is an object of another embodiment herein to suppress an immune response in a subject in need of said suppressing, e.g., where the immune response is part of an inflammatory response. This method comprises administering to a subject in need of said suppressing of an immunosuppressive effective amount, e.g., an inflammation ameliorating amount of compound of the invention herein.

It is an object of still another embodiment herein to provide a method of prophylaxis or treatment of a subject for a stroke. This method comprises administering to said subject of a therapeutically effective amount, e.g., a neuronal cell protecting amount, of a compound of the invention herein.

The term "subject" is used herein to mean any mammal, including humans, where nitric oxide formation from arginine occurs.

The term "prophylaxis" is used herein to mean to prevent or delay the occurrence of a condition or to ameliorate the symptoms of a condition should it occur compared to where prophylaxis is not carried out.

DETAILED DESCRIPTION

We turn now in more detail to the novel compounds herein.

As indicated above, one group of compounds herein consists of those where none of R, R' and R" provides an alkyl substituent on ornithine or lysine moiety. Where this is the case, the compounds herein are those including ornithine or lysine moieties without monoalkyl carbon-substitution thereon. Ornithine moiety is the case where x equals zero. Lysine moiety is the case where x is 1.

As indicated above, another group of compounds herein consists of those where one of R, R' and R" provides an alkyl substituent on ornithine or lysine moiety. Where this is the case, the compounds herein are those including monoalkyl carbon-substituted ornithine or lysine moieties. Monoalkyl carbon-substituted ornithine moiety is the case where x equals zero. Monoalkyl carbon-substituted lysine moiety is the case where x is 1.

We turn now to the moiety Q. A heme molecule is depicted below, wherein iron may be in the ferrous ($Fe^{+2}$) or in the ferric ($Fe^{+3}$) state.

A heme binding moiety Q binds to the ferrous or ferric iron in the heme molecule. This binding is supported by spectral data in Example V herein. Preferred heme binding moieties Q contain sulfur. Very preferably, heme binding moieties Q contain sulfide, sulfhydryl, thiono or thienyl sulfur and the sulfur atom of these binds to the iron. Heme binding moieties Q besides those containing sulfur include imidazole and substituted imidazoles, pyrrole, and selenium. Arginine antagonists heretofore have not included a heme binding moiety; e.g., $N^G$-methyl-L-arginine does not contain a heme binding moiety.

Very preferably Q is selected from the group consisting of =S, —$CH_2SH$, —$CH_2CH_2SH$, —$NHCH_2SH$, —$NHCH_2CH_2SCH_3$, Most preferably Q is =S or thienyl.

Examples of Specific compounds having the structural formula set forth above where none of R, R' and R" provides an alkyl substituent on ornithine or lysine moiety are (1) Thiocitrulline (where x is zero and Q is =S). This is prepared as set forth in Example I.

(2) $N^\delta$-2-Thioethylimino-L-ornithine (where x is zero and Q is —$CH_2SH$). This may be prepared by reacting L-ornithine with ethyl 2-S-benzylthioethylimidate (i.e., $C_6H_5CH_2SCH_2CH$=$NH(OC_2H_5)$), followed by sodium/liquid ammonia reduction to remove the S-benzyl group. The required imidate is prepared by reacting 2-S-benzylthioacetonitrile with ethanol and HCl. The required substituted acetonitrile may be obtained by reacting commercially available 2-chloro- or 2-bromoacetonitrile with benzylmercaptan.

(3) $N^\delta$-3-Thiopropylimino-L-ornithine (where x is zero and Q is —$CH_2CH_2SH$). This may be prepared by reacting L-ornithine with ethyl 2-S-benzylthiopropylimidate (i.e., $C_6H_5CH_2SCH_2CH_2$, CH=$NH(OC_2H_5)$), followed by sodium/liquid ammonia reduction to remove the S-benzyl group. The required imidate is prepared by reacting 3-S-benzylthiopropylnitrile with ethanol and HCl. The required substituted propylnitrile may be obtained by reacting acrylonitrile with benzylmercaptan.

(4) $N^G$-2-Thioethyl-L-arginine (where x is zero and Q is —$NHCH_2CH_2SH$). This may be prepared by reacting N$^\alpha$-(tert-butyloxycarbonyl)-δ-(S-methylthiopseudoureido)-L-norvaline tert-butyl ester with S-benzylcysteamine. S-Benzylcysteamine is prepared by reacting cysteamine with benzyl chloride at pH 8.5–9.5; under these conditions the sulfur is far more reactive than the amino group. The norvaline derivative is prepared from N$^\alpha$-(tert-butyloxycarbonyl)-δ-(thioureido)-L-norvaline tert-butyl ester by reaction with methyliodide to form the S-methylthiopseudouronium compound.

(5) N$^G$-2-Methylmercaptoethyl-L-arginine (where x is zero and Q is —NHCH$_2$CH$_2$SCH$_3$). This may be prepared by the method outlined above in (4) with the modification that methyl iodide is used in place of benzyl chloride in the reaction with cysteamine.

(6) N$^δ$-(2-Thienyl)methylimino-L-ornithine (where x is zero and Q is

This is prepared as set forth in Example III.

(7) N$^δ$-(2-Thienyl)ethylimino-L-ornithine (where x is zero and Q is

This may be prepared as described in Example III except that 2-(2-thiophene)-acetonitrile is substituted for 2-thiophenecarbonitrile.

(8) Homothiocitrulline (where x is 1 and Q is ═S). This is prepared as set forth in Example II.

(9) N$^ε$-2-Thioethylimino-L-lysine (where x is 1 and Q is —CH$_2$SH). This may be prepared as set forth in (2) above except that L-lysine is substituted for L-ornithine.

(10) N$^ε$-2-Thiopropylimino-L-lysine (where x is 1 and Q is —CH$_2$CH$_2$SH). This may be prepared as set forth in (3) above except that L-lysine is substituted for L-ornithine.

(11) N$^G$-2-Thioethyl-L-homoarginine (where x is 1 and Q is —NHCH$_2$CH$_2$SH). This may be prepared as set forth in (4) above except that L-lysine is substituted for L-ornithine.

(12) N$^G$-2-Methylmercaptoethyl-L-homoarginine (where x is 1 and Q is —NHCH$_2$CH$_2$SCH$_3$). This may be prepared as set forth in (5) above except that L-lysine is substituted for L-ornithine.

(13) N$^ε$-(2-Thienyl)ethylimino-L-lysine (where x is 1 and Q is

This may be prepared as set forth in (6) above except that L-lysine is substituted for L-ornithine.

(14) N$^ε$-(2-Thienyl)propylamino-L-lysine (where x is 1 and Q is

This may be prepared as set forth in (7) above except that L-lysine is substituted for L-ornithine.

Examples of specific compounds where one of R, R' and R" provides an alkyl substituent on ornithine or lysine moiety are:

(15) α-Methyl-DL-thiocitrulline (where R is CH$_3$, R' is CH$_2$ and R" is CH$_2$, and x is zero and Q is ═S). This compound may be prepared by using α-methyl-DL-ornithine in place of L-ornithine in Example I. α-Methyl-DL-ornithine is commercially available from Sigma Chemicals, St. Louis, Mo.

(16) β-Methyl-DL-thiocitrulline (where R is H, R' is C(H)(CH$_3$) and R" is CH$_2$ and x is zero and Q is ═S). This compound may be prepared by using β-methyl-DL-ornithine in place of L-ornithine in Example I. β-Methyl-DL-ornithine is prepared by reacting diethylacetamidomalonate with crotononitrile, followed by catalytic hydrogenation of the nitrile group to an amino group. Treatment of that intermediate in boiling acid results in the deesterification and decarboxylation of the original malonate moiety yielding in β-methyl-DL-ornithine.

(17) γ-Methyl-DL-thiocitrulline (where R is H, R' is CH$_2$ and R" is C(H)(CH$_3$) and x is zero and Q is ═S). This compound may be prepared by using γ-methyl-DL-ornithine in place of L-ornithine in Example I. γ-Methyl-DL-ornithine is prepared as described above for β-methyl-DL-ornithine except methacrylonitrile is substituted for crotononitrile.

(18) α-Methyl-DL-homothiocitrulline (where R is CH$_3$, R' is CH$_2$ and R" is CH$_2$ and x is 1 and Q is ═S). This compound may be prepared by using α-methyl-DL-lysine in place of L-lysine in Example II. The α-alkyl lysines are prepared from the β-ketonitrile having the structure R—CO—CH$_2$—CH$_2$—CH$_2$—CN, where R is the alkyl group (e.g., methyl) by Strecker amino acid synthesis and reduction of the nitrile group by catalytic hydrogenation followed by hydrolysis.

(19) β-Methyl-DL-homothiocitrulline (where R is H, R' is C(H) (CH$_3$) and R" is CH$_2$ and x is 1 and Q is ═S). This compound may be prepared by using β-methyl-L-lysine in place of L-lysine in Example II. The β-alkyl lysines are prepared in the same way as the β-alkyl ornithines except that γ-bromo-γ-alkyl butyronitrile is used in placed of the β-substituted acrylonitrile and 1M equivalent of base (e.g., sodium methoxide) is included in the reaction mixture. Alternative syntheses of β-alkyl lysines are well known in the literature.

(20) γ-Methyl-DL-homothiocitrulline (where R is H, R' is CH$_2$ and R" is C(H) (CH$_3$) and x is 1 and Q is ═S). This compound may be prepared by using γ-methyl-L-lysine in place of L-lysine in Example II. The γ-alkyl lysines are prepared in the same way as the γ-alkyl ornithines except that β-alkyl-γ-bromobutyronitrile is used in place of the α-substituted acrylonitrile and 1M equivalent of base (e.g., sodium methoxide) is included in the reaction mixture. Alternative synthesis of γ-alkyl lysines are well known in the literature.

Syntheses of β-methyl-DL-ornithine, γ-methyl-DL-ornithine, α-methyl-DL-lysine, β-methyl-DL-lysine and γ-methyl-DL-lysine are described in Griffith U.S. patent application Ser. No. 07/889,345. L-Enantiomers can be made by using L-enantiomer reactants. D,L-Compounds can be made by using D,L-reactants. Admixtures of 50 to 100% L-enantiomer with the remainder being D-enantiomer can be prepared by admixing L-compound with D,L-compound. Admixtures containing less than 50% L-enantiomer can be made by synthesizing D-enantiomer (by starting with D-compound reactant) and admixing this with L-compound or D,L-compound.

The compounds herein are not biologically active as arginine analogs with respect to protein synthesis. Therefore, there is no possibility of these interfering with incorporation of arginine into proteins.

We turn now to the methods herein.

As previously indicated, embodiments herein are directed to methods of treatment of a subject for systemic hypotension caused by pathological overproduction of nitric oxide from arginine by the enzyme nitric oxide synthase induced in vascular smooth muscle or endothelial cells in said subject with a cytokine or by a bacterial endotoxin. The inducement by cytokines, e.g., gamma-interferon, tumor necrosis factor, interleukin-1 or interleukin-2 can occur because of therapy with said cytokines, e.g., chemotherapeutic treatment with tumor necrosis factor or interleukin-2. In such therapy, the cytokine is administered in conventional amounts for said therapy. However, whereas the period for administration of said therapy is normally limited by the eventual occurrence of severe hypotension and vascular leak, the method herein allows concomitant administration of compound of the invention herein (the term prophylaxis includes said concurrent administration) to delay or eliminate the occurrence of these symptoms. The inducement by endotoxin from bacterial infection or other bacterial toxin is known as septic shock and is the leading cause of death in intensive care units, some 250,000 deaths in one year recently in the U.S. This can be an expected condition in cases where the immune system is compromised, e.g., because of immunosuppression therapy or in AIDS. Septic shock also occurs in immunocompetent people.

We turn now to the method herein for prophylaxis or treatment of a subject for systemic hypotension caused by biological overproduction of nitric oxide from arginine by nitric oxide synthase induced in vascular smooth muscle or endothelial cells in said subject with a cytokine or by a bacterial endotoxin wherein the method comprises administering to said subject a therapeutically effective amount of a compound of the invention herein. For treatment of systemic hypotension which is already occurring, the compound is administered in a blood pressure raising amount, generally 1 mg/kg to 100 mg/kg for L-enantiomer (preferably 2 mg/kg to 20 mg/kg for L-thiocitrulline and 2 mg/kg to 20 mg/kg for L-homothiocitrulline) by a route of administration obtaining a fast response, normally parenteral, preferably intravenous. For treatment in cases where systemic hypotension is expected (i.e., for prophylaxis, i.e., prevention or delay of the condition occurring or to provide ameliorated occurrence of the condition), administration is to provide a plasma level of compound of invention herein sufficient to eliminate or delay the occurring of the hypotension or to reduce the severity of the hypotension which occurs, generally a plasma concentration ranging from 1 µM to 100 µM for L-enantiomer (preferably 10 µM to 50 µM for L-thiocitrulline and 10 µM to 50 µM for L-homothiocitrulline) by a route of administration which can be parenteral (e.g., intravenous) but also can be oral (doses to provide this concentration may be determined by considering the half-life of the compounds in the body).

We turn now to the method herein for treatment of a subject for systemic hypotension caused by pathological overproduction of nitric oxide from arginine by nitric oxide synthase induced in vascular smooth muscle or endothelial cells in said subject with a cytokine or by a bacterial endotoxin wherein the method comprises administering to a subject in need of said treatment of a conventional amount of at least one $\alpha_1$ adrenergic agonist and an amount of compound of the invention herein effective to restore vascular contractile sensitivity to the effects of said $\alpha_1$ adrenergic agonists. The $\alpha_1$ adrenergic agonists are used for the same purpose now (i.e., to increase blood pressure in a hypotensive patient) but eventually stop working because of loss of vascular contractile sensitivity. The $\alpha_1$ adrenergic agonists are used in the same dosages as they are used now for the same purpose, i.e., in conventional therapeutically effective amounts. Suitable $\alpha_1$ adrenergic agonists are epinephrine, norepinephrine, dopamine, phenylephrine, metaraminol, methoxamine, ephedrine, nephentermine and angiotensin II. Doses for dopamine typically range from 2 µg/kg/min to 50 µg/kg/min. Doses for epinephrine typically range from 0.25 mg to 1.0 mg. Doses for norepinephrine typically range from 2 µg/min to 4 µg/min and are typically used if dopamine dose exceeds 20 µg/kg/min. Doses for phenylephrine can range from 0.1 to 10 µg/kg. Doses for angiotensin II can range from 0.01 to 1 µg/kg. The route of administration of the most popular $\alpha_1$ adrenergic agonists (epinephrine, norepinephrine and dopamine) is intravenous and for the others the route of administration is intravenous or in some cases subcutaneous. The compound of the invention herein is administered in an amount effective to restore vascular contractile sensitivity to the effects of the $\alpha_1$ adrenergic agonist (i.e., to increase and/or prolong the efficacy of the $\alpha_1$ adrenergic agonists), generally 1 mg/kg to 100 mg/kg for L-enantiomer (preferably 2 mg/kg to 20 mg/kg for L-thiocitrulline and 2 mg/kg to 20 mg/kg for L-homothiocitrulline) by a route of administration obtaining a fast response, normally parenteral, preferably intravenous.

We turn now to the method herein for suppressing an immune response, e.g., where the immune response is part of an inflammatory response, in a subject in need of said suppressing, said method comprising administering to a subject in need of said suppressing an immunosuppressive effective amount of compound of the invention herein. This method may be directed to prophylaxis or treatment of a subject for inflammation, e.g., arising from autoimmune conditions including rheumatoid arthritis and from host-defense immune mechanisms, e.g., allograft rejection reactions, caused by immunologically induced nitric oxide production in immune cells, said method involving inhibiting said nitric oxide production in said cells by administering to a subject possibly developing or having such inflammation, a nitric oxide synthesis inhibiting therapeutically effective amount of compound of the invention herein. The dosages of L-enantiomer compound herein for use in this method generally range from 1 mg/kg to 1000 mg/kg (preferably 2 mg/kg to 200 mg/kg for L-thiocitrulline and 2 mg/kg to 200 mg/kg for L-homothiocitrulline). Methods of administration include oral, intramuscular, subcutaneous and intravenous. The dosages set forth above are daily dosages and are administered for a period of time to cause suppression of immune response and attenuation of inflammation, i.e., two days or more, e.g., for two to three weeks.

We turn now to the method herein for prophylaxis or treatment of a subject for a stroke wherein the method comprises administering to said subject of a therapeutically effective amount of compound of the invention herein. For a stroke in progress, administration is preferably within 6 hours of the onset of the stroke, very preferably within 4 hours of the onset of the stroke. Since time is of the essence, administration typically is as soon as practical after diagnosis. The therapeutically effective amount is a neuronal cell protecting amount, i.e., an amount which causes increase in neuronal cell survival compared to where the stroke is untreated. Generally, the dose for L-enantiomer ranges from 1 mg/kg to 100 mg/kg (preferably 2 mg/kg to 20 mg/kg for L-thiocitrulline and 2 mg/kg to 20 mg/kg for L-homothiocitrulline). Administration is by a route offering a fast response, e.g., parenteral, preferably intravenous or intraarterial. Prophylaxis involves treatment of those of high risk for a stroke because of medical history and administration is that amount sufficient to provide an uninterrupted plasma level of compound herein in a neuronal cell protecting concentration, generally 1 µM to 100 µM for L-enantiomer (preferably 10 µM to 50 µM for L-thiocitrulline and 10 µM to 50 µM for L-homothiocitrulline) and administration is preferably carried out orally on a daily basis.

Dosages are given above for the L-enantiomer. For admixtures of L-enantiomer and D-enantiomer, dosages are calculated by dividing those given above by the weight percent of L-enantiomer in the admixture.

The invention is illustrated in the following examples.

EXAMPLE I

Synthesis of L-Thiocitrulline $N^\delta$-(Benzyloxycarbonyl)-L-ornithine tert-butyl ester was prepared according to a general published procedure (Bodanszky, M.; Bodanszky, A.; The Practice of Peptide Synthesis; Spring Verlag: New York, 1984). Specifically, $N^\delta$-(benzyloxycarbonyl)-L-ornithine (10.0 gm, 37.6 mmol, Sigma Chemicals, Inc.) was mixed with tert-butyl acetate (564 ml) and perchloric acid (5.91 ml, 69–72% aqueous solution) at room temperature. The reaction mixture became homogenous after 15 minutes and was stirred at room temperature for 2 days. Water (300 ml) was added to the reaction mixture, and the two layers obtained were separated. The organic layer was extracted twice (2×200 ml) with water, and the combined aqueous layers were adjusted to pH 9.5–10.0 with 50% NaOH. The aqueous layer was then filtered to remove a small amount of insoluble material, and the filtrate was extracted with ethyl acetate (3×300 ml). The combined ethyl acetate extracts were dried over $MgSO_4$ and were concentrated by rotary evaporation at reduced pressure to yield 7.5 g of $N^\delta$-(benzyloxycarbonyl)-L-ornithine tert-butyl ester as an oil (65% yield). $^1H$ NMR ($DCCl_3$) δ 1.44 (s,9H), 1.5–1.9 (m,4H), 3.23 (t,2H), 3.31 (t,1H), 5.09 (s,2H and s,1H broad), 7.35 (s,5H).

$N^\alpha$-(tert-Butyloxycarbonyl)-$N^\delta$-(benzyloxycarbonyl)-L-ornithine tert-butyl ester $N^\delta$-(Benzyloxycarbonyl-L-ornithine tert-butyl ester (7.50 g, 23.3 mmol) was dissolved in 27 ml of methylene chloride, and the solution was cooled to 0° C. To that solution was added dropwise tert-butyl pyrocarbonate (5.87 g, 26.9 mmol) in 10 ml of methylene chloride. The reaction mixture was stirred at 0° C. for 1 hour, and stirring was continued for 3 additional hours at room temperature. The solvent was evaporated at reduced pressure and the oily residue was chromatographed on a column of silica gel (25 cm×30 mm) using hexane:ethyl acetate (3:1) as solvent. Fractions of approximately 5 ml were collected, and those containing product were identified by thin layer chromatography (see below). Chromatographic fractions containing product were pooled and evaporated to a thick oil by rotary evaporation at reduced pressure. The yield was 8.63 gm (93.5%). $^1H$ NMR ($DCCl_3$) δ1.44 (s,9H), 1.46 (s,9H), 1.5–1.9 (m,4H), 3.23 (t,2H), 4.17 (t,1H), 4.88 (s,1H broad), 5.09 (s,2H and s,1H broad) 7.35 (s,5H).

Thin layer chromatography was carried out on silica gel plates using hexane:ethyl acetate (3:1) as solvent. $N^\delta$(benzyloxycarbonyl)-$N^\alpha$-(tert-butyloxycarbonyl)-L-ornithine tert-butyl ester chromatographed with an $R_f$=0.33 and was detected by fluorescence using a hand-held UV light.

$N^\delta$-tert-butyloxycarbonyl-L-ornithine tert-butyl ester

The ester from the previous step (8.63 gm, 20.45 mmol) was dissolved in 50 ml of methanol and 10% Pd/C catalyst (0.90 gm) was added. The mixture was hydrogenated on a Parr hydrogenator at 20 psi $H_2$ for 4 hr. Following reduction, the reaction mixture was filtered over Celite and evaporated to dryness by rotary evaporation at low pressure to provide $N^\alpha$-(tert-butyloxycarbonyl)-L-ornithine tert-butyl ester as an oil. The yield was 5.88 gm (100%). $^1H$ NMR ($DCCl_3$) δ 1.44 (s,9H), 1.46 (s,9H), 1.5–1.9 (m,4H), 2.73 (t,2H), 4.17 (t, 1H), 5.20 (s,1H broad).

$N^\alpha$-(tert-butyloxycarbonyl)-δ-(thioureido)-L-norvaline tert-butyl ester This product was prepared as described by Feldman (Feldman, P. L.; Tetrahedron Lett. 1991, 32, 875–878). $N^\alpha$-(tert-butyloxycarbonyl)-L-ornithine tert-butyl ester (5.80 gm) was dissolved in 100 ml chloroform and added to a solution of 5.70 gm of calcium carbonate and 2.2 ml of thiophosgene (28.7 mmol) dissolved in 100 ml of water. The mixture was stirred vigorously overnight. The next day the reaction mixture was filtered and the layers were allowed to separate. The aqueous layer was extracted with chloroform (2×50 ml) and the combined organic layers were dried ($MgSO_4$) and concentrated to an oil by evaporation at reduced pressure. The residue was taken up in dry methanol (200 ml) and cooled to 0° C. Ammonia gas was then passed through the solution for 20 minutes, and the solution was stirred for 3 hours at 0° C. Following reaction with ammonia, the solvent was evaporated under reduced pressure and the residue was dissolved in ethyl acetate:hexane (4:1). That solution was chromatographed on a column of silica gel (25 cm×30 mm) using the same ethyl acetate/hexane mixture as eluent. Fractions of approximately 5 ml were collected, and those containing product were identified by thin layer chromatography (see above, $R_f$=0.30). Product-containing fractions were pooled and evaporated to dryness under reduced pressure to yield $N^\alpha$-(tert-butyloxycarbonyl)-δ-(thioureido)-L-norvaline tert-butyl ester in 70% yield. $^{13}C$ NMR ($DCCl_3$) 183.4–180.4 (one carbon), 17.1–6, 155–9, 82.2–80.0, 53.6 –52.5 (one carbon), 44.6–43.1 (one carbon), 30.4, 28.1, 27.8, 24.6.

$N^\delta$-(Thioureido)-L-norvaline (L-Thiocitrulline)

$N^\alpha$-(tert-butyloxycarbonyl)-δ-(thioureido)-L-norvaline tert-butyl ester was mixed with a solution of 4N hydrochloric acid in dioxane and kept at room temperature for 24 hours. A solid precipitate formed. The mixture was then diluted with ethyl ether (20 ml) and the entire solution was evaporated to dryness under reduced pressure. Methanol (10 ml) was added and evaporated at reduced pressure 2 to 3 times to provide $N^\delta$-thioureido-L-norvaline, called L-thiocitrulline, as a white solid. The yield was 600 mg, 91%. $^1$H NMR (CD$_3$OD) δ 1.40–1.90 (m,4H), 3.16 (t,2H), 3.74 (t,1H); $^{13}$C NMR (CD$_3$OD) δ 25.40, 28.69, 44.53, 53.47, 171.48; (IR (KBr) cm$^{-1}$: 1710, 1635, 1595, 1470, 1390, 1300; mass spectrum, 192 (MH+).

REFERENCE EXAMPLE I

D-Thiocitrulline was prepared as described for L-thiocitrulline (Example I) except that the starting material was N$^δ$-(benzyloxycarbonyl)-D-ornithine (Sigma Chemicals, Inc.). Starting with 5.0 gm of that material the final yield of D-thiocitrulline was 600 mg (29% overall yield).

EXAMPLE II

Synthesis of N$^ε$-(Thioureido)-L-norleucine (L-Homothiocitrulline). N$^α$-(Benzyloxycarbonyl)-L-lysine tert-butyl ester N$^α$-(Benzyl-oxycarbonyl)-L-lysine (5.0g m, 17.84 mmol) was dissolved in 268 ml of tert-butyl acetate containing 2.80 ml of perchloric acid (69–72% aqueous solution). The solution was stirred for 2 days at room temperature and then was extracted with water (3×200 ml). The combined aqueous layers were adjusted to pH 10 with 50% sodium hydroxide. The aqueous solution was then extracted with ethyl acetate (3×200 ml) and the organic layers dried over MgSO$_4$. After filtration to remove MgSO$_4$, the solvent was removed by evaporation at reduced pressure to provide N$^α$-(benzyloxycarbonyl)-L-lysine tert-butyl ester as a clear oil (2.16 gm, 36%). $^1$H NMR (CDCl$_3$) 1.35 (s,9H), 1.40–2.0 (m,6H), 2.60 (t,2H), 4.10 (m,1H), 4.98 (s,2H), 5.29 (bs,1H), 7.35 (s,5H).

N$^ε$-(thioureido)-N$^α$-(Benzyloxycarbonyl)-L-norleucine

N$^α$-(benzyoxycarbonyl)-L-lysine tert-butyl ester (2.16 gm, 6.43 mmol) was dissolved in 30 ml of chloroform and added to a prepared solution of calcium carbonate (1.80 g, 18.0 mmol) in 30 ml of water containing 0.70 ml of thiophosgene; the mixture was stirred for 6 hours at room temperature. The reaction mixture was then filtered and the layers separated. The aqueous layer was extracted with chloroform (2×30 ml) and the combined organic layers were dried over MgSO$_4$. After filtration to remove MgSO$_4$, the dry solution was evaporated under reduced pressure to yield a clear oil. The residue was dissolved in 55 ml of methanol and cooled to 0° C. Ammonia gas was passed into the solution for 15 minutes and the reaction mixture was stirred for 3 hours at 0° C. The methanol was then evaporated at reduced pressure and the residue was chromatographed on a column of silica gel (25 cm×30 mm) using ethyl acetate-:hexane (4:1) (R$_f$=0.33) as the eluent. Fractions containing product were identified by thin layer chromatography and were pooled. Evaporation of the product-containing fractions yielded N$^α$-(benzyloxycarbonyl)-N$^ε$-thioureido-L-norleucine tert-butyl ester as a foamy solid. $^{13}$C NMR (CDCl$_3$) δ 182.70–179.6 (one carbon), 171.35, 155.99, 135.77, 129.19, 128.85, 127.08, 126.61, 81.92, 68.5–64.65 (one carbon) 54.73–52.97 (one carbon), 46.30–41.50 (one carbon), 30.10, 28.40, 26.73, 25.0.

N$^ε$-(thioureido)-L-norleucine (L-Homothiocitrulline)

N$^ε$-(carbobenzoxy)-ε-thioureido-L-norleucine (1.31 g, 3.32 mmol) was dissolved in 4N HCl/dioxane (12 ml) and heated to 75° C. for 1 hour and left at room temperature for 3 hours. The reaction mixture was diluted with ether (20 ml) and the solvents were evaporated under reduced pressure. This was repeated two times. Methanol (10 ml) was then added and the solvent was evaporated under reduced pressure to provide N$^ε$-thioureido-L-norleucine, called L-homothiocitrulline, as a white solid (900 mg, 93%).

EXAMPLE III

Synthesis of N$^δ$-(2-thienyl)methylimino-L-ornithine

O-Methyl 2-thienylmethylimidate was prepared by mixing 2-thiophenecarbonitrile (Aldrich Chemicals, 10.0 g, 0.092 mol) with methanol (3.73 ml, 0.092 mol) and cooling to 0° C. with stirring. HCl gas was passed through the solution for 15 minutes, and the reaction mixture was then left in the refrigerator overnight. During storage, a solid white precipitate formed, and it was triturated With ether (50 ml). That suspension was filtered, and the while solid was washed with ether (2×50 ml) and dried under vacuum over potassium hydroxide. The yield of methyl 2-thienylmethylimidate HCl was 13.1 g (80%).

N$^δ$-(2-Thienyl)methylimino-L-ornithine was prepared by reaction of the previously described imidate with the copper salt of L-ornithine. Specifically, L-ornithine HCl (1.69 g, 10 mmol) and cupric acetate (1.0 g, 5 mmol) were dissolved in 13 ml of water, and the solution was cooled to 0° C. The pH of the solution was adjusted to 9.65 with sodium hydroxide. To that stirred solution was added 2-thienylmethylimidate HCl (2.84 g, 16 mmol) in small portions; the pH was kept between 9.5 and 10 by addition of small aliquots of 50% sodium hydroxide. The reaction mixture was stirred at 0° C. for 2 hours and then at room temperature for 1 hour. The reaction mixture became turbid and a precipitate formed. The pH was adjusted to 7 and 100 ml of water was added to dissolve the solid. The resulting solution was applied to a column of Dowex-50 (NH$_4^+$, 200–400 mesh, 2.5×30 cm). The resin was washed with 500 ml of water and then with 0.1M ammonium hydroxide (1 L). The product was eluted with 5M ammonium hydroxide solution. Two 500 ml fractions were collected and evaporated to a clear oil under reduced pressure. The residue was dissolved in a minimum amount of water (50 ml) and the pH was adjusted to 7 with HCl. The resulting solution was again concentrated to dryness by rotary evaporation at reduced pressure, and ethanol (20 ml) was added. Repeated evaporation of the solution to dryness at reduced pressure resulted in formation of a white solid which gave an NMR spectra consistent with N$^δ$-(2-thienyl) methylimino-L-ornithine. The yield was 1.30 g (54%). $^1$H NMR (D$_2$O) δ 1.65–1.75 (m,4H), 2.84 (t,2H), 3.50 (5,1H), 7.06 (m,1H), 7.60–7.70 (m,2H); mass spectrum, 243 (MH$^+$).

EXAMPLE IV

Ki of L-Thiocitrulline Determined with the Rat Brain Nitric Oxide Synthase

Figure 1:
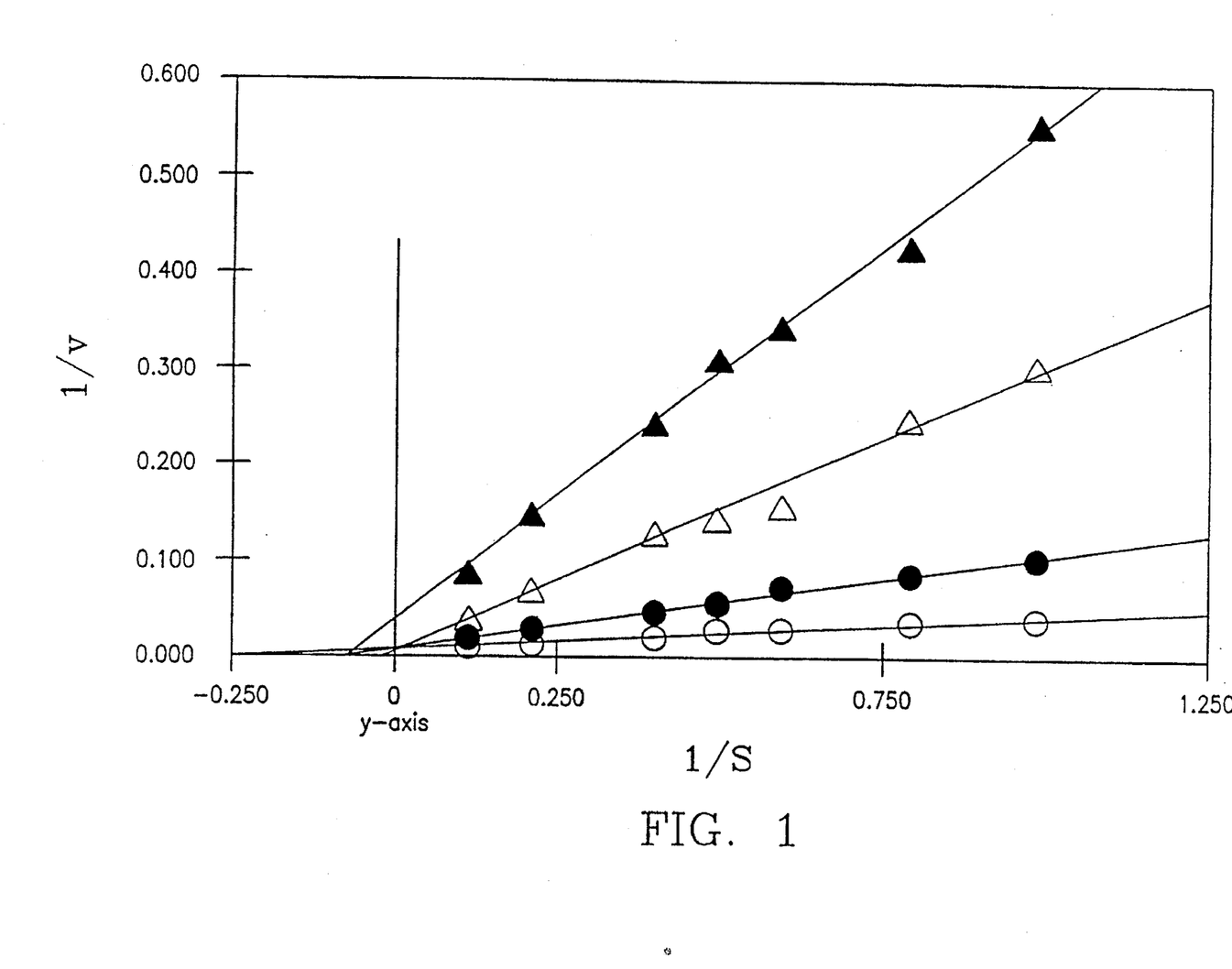
FIG. 1 is a Lineweaver-Burk plot of the reciprocal of the observed reaction velocity (1/v) versus the reciprocal of the concentration of substrate arginine (1/S) for the Ki determination of Example IV.

To determine the binding affinity of L-thiocitrulline to rat brain nitric oxide synthase, rate measurements were made at several concentrations of L-arginine (1 to 10 μM) in the absence or the presence of L-thiocitrulline (1, 3, or 5 μM). The reaction mixtures were identical to those described in Example X except that the final volume was 50 μl and only a single time point (5 min) was taken. In FIG. 1, the line denoted by filled in triangles is for measurements for 5 μM L-thiocitrulline, the line denoted by open triangles is for measurements for 3 μM L-thiocitrulline, the line denoted by filled in circles is for 1 µM L-thiocitrulline and the line denoted by open circles is for no L-thiocitrulline and the Y-axis is the vertical line extending upwardly from 0. As shown in FIG. 1, increasing concentrations of L-thiocitrulline caused increasing degrees of inhibition. The graph shown is a Lineweaver-Burk plot in which the reciprocal of the observed reaction velocity (1/v) is plotted versus the reciprocal of the concentration of substrate arginine (1/S). Results obtained at concentrations of 1 µM, 3 µM and 5 µM L-thiocitrulline, and results obtained in the absence of L-thiocitrulline, were plotted to give individual lines as shown. In such a graph, intersection of all lines on the Y-axis would indicate purely competitive inhibition, whereas the intersection of the lines on the X-axis would indicate purely non-competitive inhibition. The actual data falls somewhere between these extremes. From the data, it is concluded that L-thiocitrulline is a competitive inhibitor but with atypical binding as evidenced by the failure of the plot to intersect exactly on the Y-axis. That means it binds similarly to substrate arginine, i.e., to the same binding site on the enzyme surface, but has some additional interaction with the enzyme. From the slopes of the line and the points of intersection, it is calculated that the Ki of L-thiocitrulline is approximately 2 µM.

EXAMPLE V

Demonstration that the Binding of Thiocitrulline to Nitric Oxide Synthase (NOS) Causes Spectral Changes Consistent with a Direct Interaction Between Inhibitor and the Iron of the Heme Cofactor In common with other heme cofactor containing enzymes, both the constitutive brain NOS and the inducible smooth muscle NOS display absorption spectra that reflect the presence of heme, the state of the iron in the heme (i.e., ferrous or ferric iron), and the interaction of ligands with the iron of heme. As isolated and examined in the absence of L-arginine, both enzymes display a peak absorbance centered near 397 nm, a small shoulder at 420 nm, and broad bands of lower extinction centered near 538 and 650 nm. All of these absorbencies indicate the presence of the heme cofactor. These spectral features are similar to those of 5-coordinate high spin heme proteins such as horseradish peroxidase and high spin-type cytochrome P-450's. When ligands such as substrate or inhibitors are bound to NOS, the spectra of the heme cofactor can change in a manner which reflects the presence or absence of direct interaction between the newly bound ligand and the heme iron. Such interactions are detected on the basis of difference spectra. That is, in a dual beam spectrophotometer the reference cuvette contains NOS in buffer whereas the sample cuvette contains NOS plus ligand (substrate or inhibitor) in buffer. The spectrophotometer is then set to scan from high to low wavelengths and will report out any differences in the absorbance of the reference and sample solutions at each wavelength examined.

When such studies are carried out with NOS and the substrate L-arginine is added to the sample cuvette, one observes that the sample cuvette shows increased absorbance at 392 nm and decreased absorbance at wavelengths greater than approximately 410 nm. Such changes are consistent with the binding of arginine in a manner in which it does not make direct interaction with the heme iron. Thus, the heme iron in the arginine-loaded enzyme has only 5 ligands. Four attachments are to the pyrrole nitrogens of the heme itself, and a fifth is a coordination which is thought to be to a sulfur belonging to a cysteine residue in the protein itself. When a similar study was carried out in which 4.5 µM L-thiocitrulline was added to a cuvette containing 3.5 µM rat brain NOS, the sample cuvette showed decreased absorption at 392 nm ($_\Delta$OD about-0.0035) and increased absorption beginning at approximately 420 nm reaching a maximum at about 440 nm. At the latter wavelength, absorption increase was approximately 0.008. These changes, which are similar but not identical to type II spectra, are interpreted as indicating that the thiocitrulline is making direct contact with the heme iron. Such spectral changes were not observed in a similar study using D-thiocitrulline, indicating that the interaction with L-thiocitrulline is stereospecific and thus attributable to the inhibitor binding to the amino acid substrate binding site. Given that L-thiocitrulline is bound as a substrate and/or product analog, the portion of the molecule in closest proximity to the heme cofactor must be the thioureido side chain. Of the possible liganding atoms involved in the thioureido side chain, only the sulfur was available to make contact with the heme iron. That is, L-citrulline, which is identical to thiocitrulline except that the sulfur is replaced by oxygen, does not give spectral changes of the type described. The side chain of citrulline contains all of the possible liganding atoms of thiocitrulline except for the sulfur.

EXAMPLE VI

Inhibition of Smooth Muscle Nitric Oxide Synthase by L-Thiocitrulline and Other Compounds The activity of L-thiocitrulline and other compounds (namely L-citrulline, D-thiocitrulline and $N^G$-methyl-L-arginine) as inhibitors of vascular smooth muscle nitric oxide synthase was determined in vitro by monitoring the conversion of [$^{14}$C]arginine to [$^{14}$C]citrulline. Smooth muscle nitric oxide synthase, an example of induced nitric oxide synthase (iNOS) was obtained as follows: aortic smooth muscle cells were cultured by explanting. segments of the medial layer of the aortae of adult male Fischer 344 rats. Aortae were removed aseptically and freed of adventitial and endothelial cells by scraping both the luminal and abluminal surfaces. Medial fragments (1–2 mm) were allowed to attach to dry Primaria 25 cm$^2$ tissue culture flasks (Falcon; Oxnard, Calif.) which were kept moist with growth medium until cells emerged. Cultures were fed twice weekly with medium 199 containing 10% fetal bovine serum, 25 mM HEPES, 2 mM L-glutamine, 40 µg/ml endothelial cell growth supplement (Biomedical Technologies; Stoughton, Mass.) and 10 µg/ml gentamyocin (GIBCO; Grand Island, N.Y.). When primary cultures became confluent, they were passed by trypsinization. Cells in passage 10–15 were seeded at 20,000/well. When the cells became confluent (density of 60–80×10$^3$ cells in a well), the medium was removed by suction and fresh medium consisting of 200 µl of RPMI 1640 (Whittaker Laboratories) containing 10% bovine calf serum, 25 mM HEPES buffer (pH 7.4), 2 mM glutamine, 80 U/ml penicillin, 80 µM/ml streptomycin, 2 µg/ml fungizone, 40 ng/ml interleukin-1 and 50 ng/ml interferon-gamma was introduced. Interleukin-1 and interferon-gamma are effective inducers of iNOS.

In a final volume of 200 µl , the reaction mixtures contained the following: 20mM sodium HEPES, pH 7.15, 0.1 mM EGTA (ethylene glycol bis(β-aminoethyl ether)-N, N,N',N'-tetraacetic acid), 0.1 mM dithiothreitol, 100 µM tetrahydrobiopterin, 500 µM NADPH, 25 µM FAD, 25 µM FMN and 0.03–0.05 units of nitric oxide synthase (1 unit equals the amount of enzyme necessary to convert 1 nmol of arginine to citrulline and nitric oxide per min). The reaction was begun by adding to the reaction mixture 20 μM L-[$^{14}$C] arginine and, except in the case of the control, 100 μM test compound (L-thiocitrulline, L-citrulline, D-thiocitrulline, and NG-methyl-L-arginine). The reaction mixtures were maintained at 25° C. and at 3.5, 7.0, and 10.5 minutes 50 μl portions were removed from each reaction mixture and added to 200 μl of 100 mM sodium HEPES, pH 5.5 containing 5 mM EGTA. The decrease in pH stops the reaction. The reaction mixtures were then placed in a boiling water bath for 1 minute which caused the protein to precipitate; the precipitate was removed by centrifugation. A 225 μl portion of the supernatant was then removed and applied to a small column of Dowex 50 (Na+ form, 200–400 mesh, 0.5×3.5 mm). L-[$^{14}$C]citrulline, a product of the reaction, was eluted from the columns using 2.0 ml of water. The eluant was collected directly into a scintillation vial, 10 ml of scintillation fluid (Econo-Safe, Research Products International Corp.) were added and the contained radioactivity was determined by liquid scintillation counting. Knowing the specific activity of the L-arginine in the original reaction mixture, it was possible to convert the cpm citrulline data to pmol product.

Figure 2:
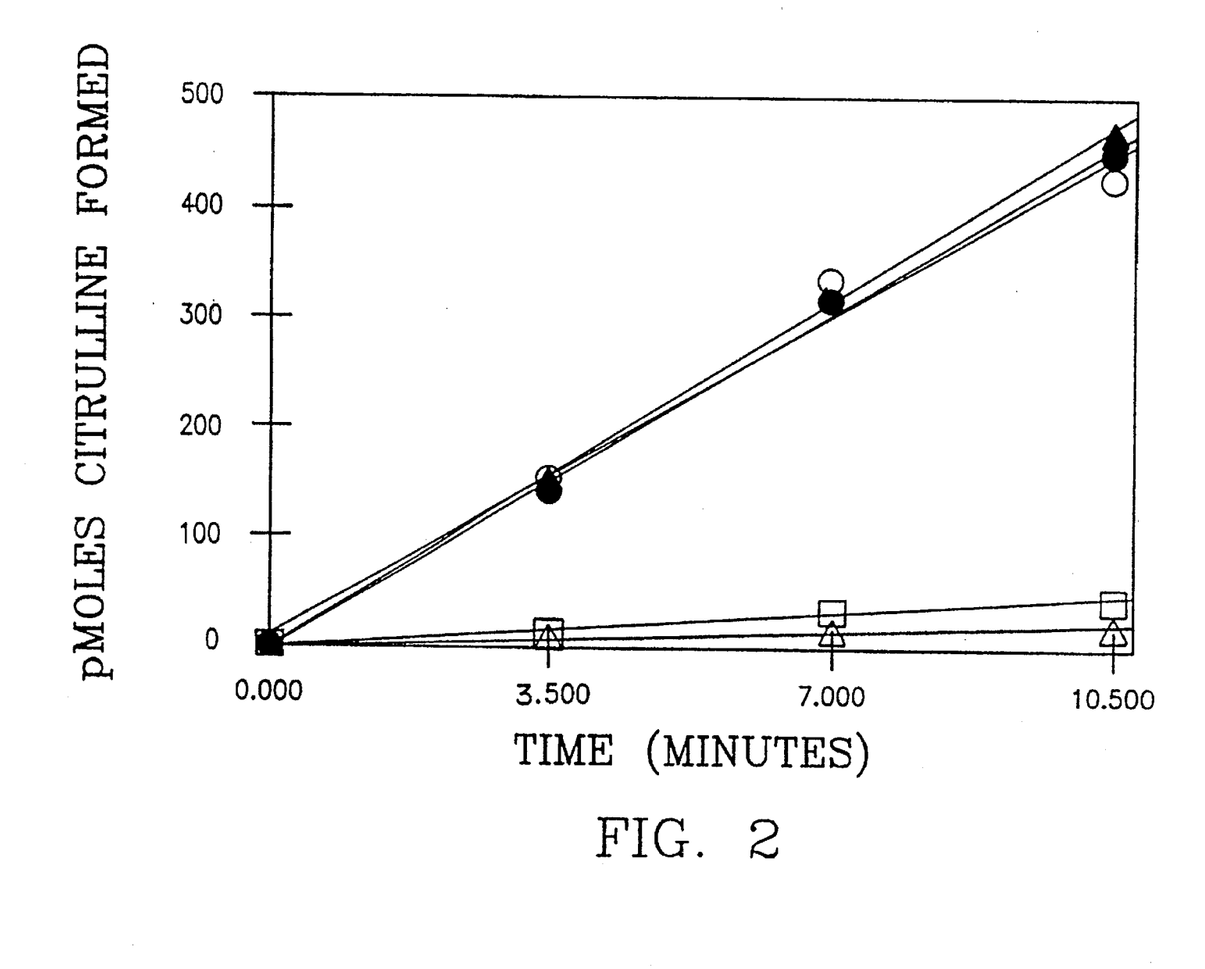
FIG. 2 is a graph of product formation versus time depicting results of Example VI.

As shown in the figure, product formation was plotted as a function of time (FIG. 2). In FIG. 2 the line denoted by open circles is the control, the line denoted by filled in circles is for the experiment with 100 μM L-citrulline, the line denoted by filled in triangles is for the experiment with 100 μM D-thiocitrulline, the line denoted by open squares is for the experiment with 100 μM N$^G$-methyl-L-arginine and the line denoted by open triangles is for the experiment with 100 μM L-thiocitrulline.

As shown in FIG. 2, in the absence of test compound (20 μM arginine control line) product formation was constant over a 10.5 minute period observed. Addition of 100 μM D-thiocitrulline or 100 μM L-citrulline caused no significant inhibition. Addition of 100 μM L-thiocitrulline caused virtually complete inhibition at all times observed. Addition of 100 μM N$^G$-methyl-L-arginine (L-NMA, the prototypic nitric oxide synthase inhibitor) also caused substantial inhibition, but NMA was somewhat less effective than L-thiocitrulline.

EXAMPLE VII

The Effect of L-Thiocitrulline on Blood Pressure

To test the ability of L-thiocitrulline to block basal nitric oxide formation in vivo, its effects were tested in anesthetized Sprague-Dawley rats. Rats (250–300 gm) were anesthetized with Inactin (100 mg/kg i.p.) and placed on a heated surgical table to maintain body temperature of 36.5° C. Femoral arterial and venous catheters were implanted (tips were distal to the renal artery) for measurement of blood pressure and infusion of compounds, respectively. Blood pressure was measured using a pressure transducer (Cobe, Inc.) connected to a microcomputer using data acquisition software (AT-CODAS; Data Q Instruments, Akron, Ohio). After waiting several minutes to establish a stable baseline blood pressure, L-thiocitrulline (20 mg/kg) was given by bolus injection through the venous catheter. The solution administered was 100 mM. Changes in systolic, diastolic, and mean arterial pressure were monitored for approximately 1 hour. Studies were carried out in 4 rats.

Initial (i.e., predrug) systolic, diastolic, and mean arterial pressures were 126±2, 83±2, and 100±3, respectively. Following administration of L-thiocitrulline, systolic, diastolic, and mean arterial pressures were 142±5, 93±4, and 115±6, respectively. There was no significant effect oh heart rate. The studies indicate that L-thiocitrulline is an effective pressor agent in vivo. Based on earlier studies with N$^G$-methyl-L-arginine, the prototypic nitric oxide synthase inhibitor, L-thiocitrulline is viewed as blocking the basal release of nitric oxide from vascular endothelial cells. Decreased release of basal nitric oxide removes an important vasodilatory mediator involved in normal blood pressure regulation and results in increased vascular tone. Increased vascular tone (vasoconstriction) increases systemic vascular resistance; blood pressure consequently increases.

EXAMPLE VII

The Effect of L-Thiocitrulline on Blood Pressure

A human is continuously administered interleukin-2 (1×10$^6$ units) for 5 days. L-Thiocitrulline (2 to 20 mg/kg/day) is administered by continuous infusion at a rate sufficient to maintain a systolic blood pressure of 80–120 mm Hg. The severe hypotension characteristic of the end of interleukin-2 therapy is significantly reduced.

EXAMPLE IX

The Effect of L-Thiocitrulline on Increasing Response to Pressor Agents

Sprague-Dawley rats are injected intraperitoneally with bacterial lipopolysaccharide (a bacterial endotoxin) (15 mg/kg) alone, together with phenylephrine (6 μg/kg), and together with L-thiocitrulline (20 mg/kg) and phenylephrine (6 μg/kg). The treatment with the combination of L-thiocitrulline and phenylephrine significantly reduces the fall in blood pressure from bacterial lipopolysaccharide administration to a greater degree than phenylephrine alone.

EXAMPLE X

Inhibition of Brain Nitric Oxide Synthase by L-Thiocitrulline and Other Compounds The activity of L-thiocitrulline and other compounds (L-citrulline, D-thiocitrulline and N$^G$-methyl-L-arginine) as inhibitors of rat brain nitric oxide synthase was determined in vitro by monitoring the conversion of [$^{14}$C]arginine to [$^{14}$C]citrulline. Purified rat brain nitric oxide synthase, isolated as described (McMillan, K., Bredt, D. S., Hirsch, D. J., Synder, S. H., Clark, J. E., and Masters, B. S., Proc. Natl. Acad. Sci. USA Vol 89, pp., 11141–11145, December 1992) was obtained from Dr. Bettie Sue Masters, The University of Texas health Science Center at San Antonio, Department of Biochemistry, 7703 Floyd Curl Drive, San Antonio, Tex. 78284.

Figure 3:
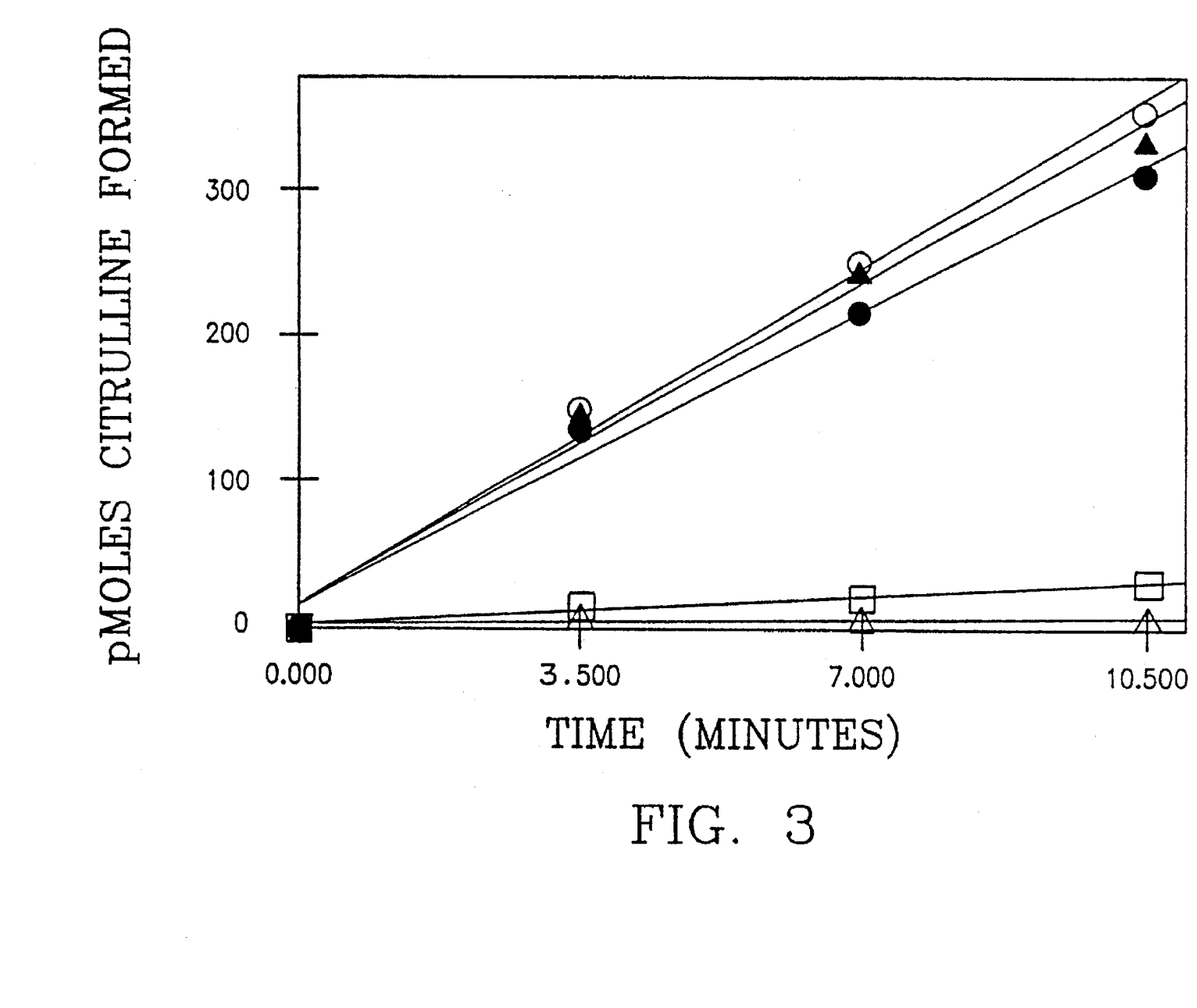
FIG. 3 is a graph of product formation versus time depicting results of Example X.

In a final volume of 200 μl , the reaction mixtures contained the following: 20 mM sodium HEPES, ph 7.5, 0.1 mM EGTA, 0.1 mM dithiothreitol, 10 μg/ml calmodulin, 2 mM calcium chloride, 100 μM tetrahydrobiopterin, 100 μg/ml bovine serum albumin, 500 μM NADPH, 25 μM FAD, 25 μM FMN and 0.03–0.05 units of nitric oxide synthase (1 unit equals the amount of enzyme necessary to convert 1 nmol of arginine to citrulline and nitric oxide per min). The reaction was begun by adding to the reaction mixture 20 μM L-[$^{14}$C]arginine and, except in the case of the control, 100 μM test compound (L-thiocitrulline, D-thiocitrulline, L-citrulline and N$^G$-methyl-L-arginine). The reaction mixtures were maintained at 25° C. and at 3.5, 7.0, and 10.5 minutes 50 μl portions were removed and added to 200 μl of 100 mM sodium HEPES, pH 5.5, containing 5 mM EGTA. The decrease in pH and the binding of calcium by EGTA stops the reaction. The reaction mixtures were then placed in a boiling water bath for 1 minute which caused the protein to precipitate; the precipitate was removed by centrifugation. A 225 μl portion of the supernatant was then removed and applied to a small column of Dowex 50 (Na+ form, 200–400 mesh, 0.5×3.5 mm). L-[$^{14}$C]Citrulline, a product of the reaction, was eluted from the columns using 2.0 ml of water. The eluant was collected directly into a scintillation vial, 10 ml of scintillation fluid (Econo-Safe, RPI Corp, Mt. Prospect, Ill.) were added and the contained radioactivity was determined by liquid scintillation counting. Knowing the specific activity of the L-[$^{14}$C]arginine in the original reaction mixture, it was possible to convert the cpm citrulline data to pmol product. As shown in FIG. 3, product formation was plotted as a function of time. In FIG. 3, the line denoted by open circles is the control, the line denoted by filled in circles is for the experiment with 100 μM L-citrulline, the line denoted by filled in triangles is for the experiment with 100 μM D-thiocitrulline, the line denoted by open squares is for the experiment with 100 μM $^G$-methyl-L-arginine and the line denoted by open triangles is for the experiment with 100 μM L-thiocitrulline.

As shown in FIG. 3, in the absence of inhibitor (20 μM arginine control line), product formation is constant over the 10.5 minute period observed. Addition of 100 μM D-thiocitrulline or 100 μM L-citrulline caused no significant inhibition. Addition of 100 μM L-thiocitrulline caused virtually complete inhibition at all times observed. Addition of 100 μM N$^G$-methyl-L-arginine (L-NMA, the prototypic nitric oxide synthase inhibitor) also caused substantial inhibition, but L-NMA was somewhat less effective than L-thiocitrulline.

EXAMPLE XI

Figure 4:
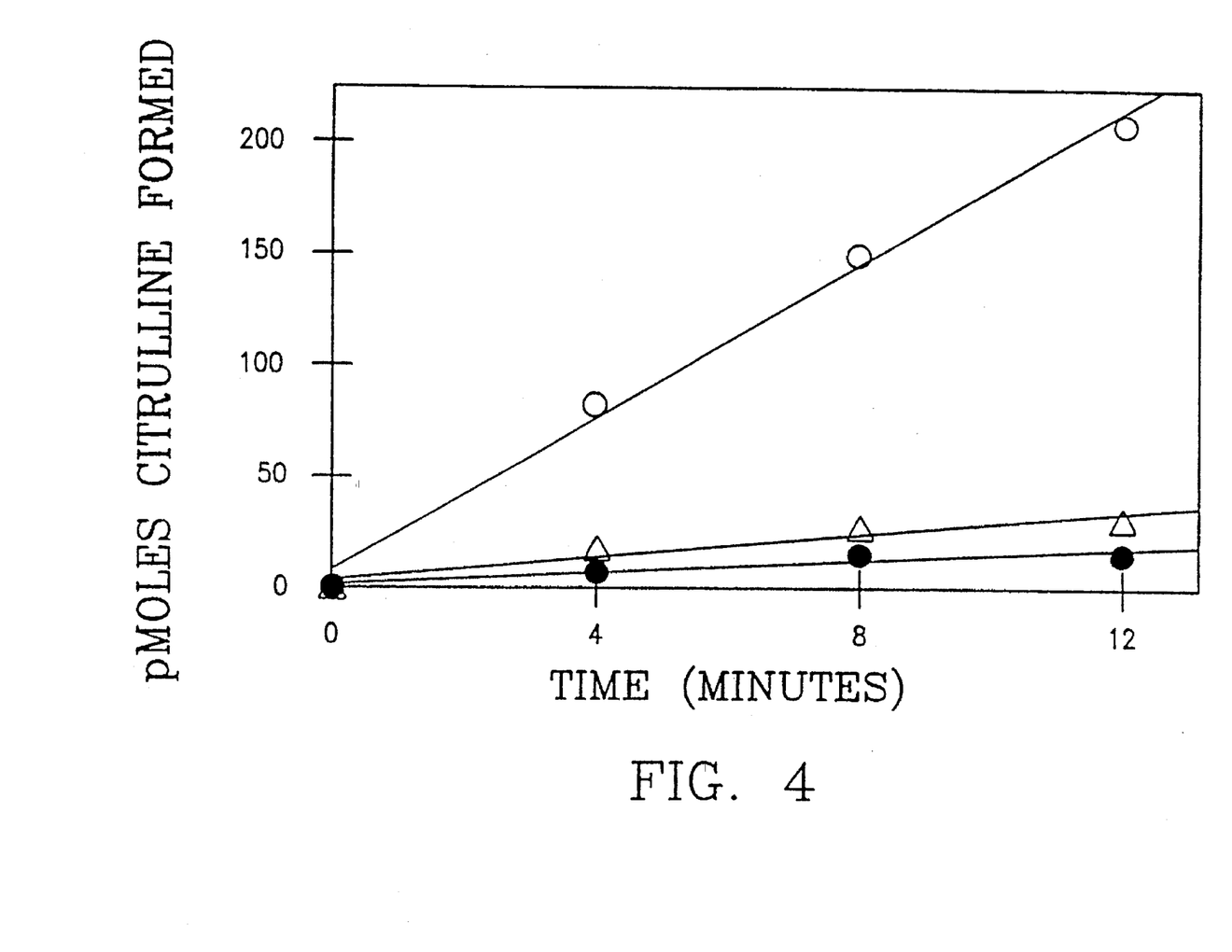
FIG. 4 is a graph of product formulation versus time depicting results of Example XI in respect to rat brain nitric oxide synthase.
Figure 5:
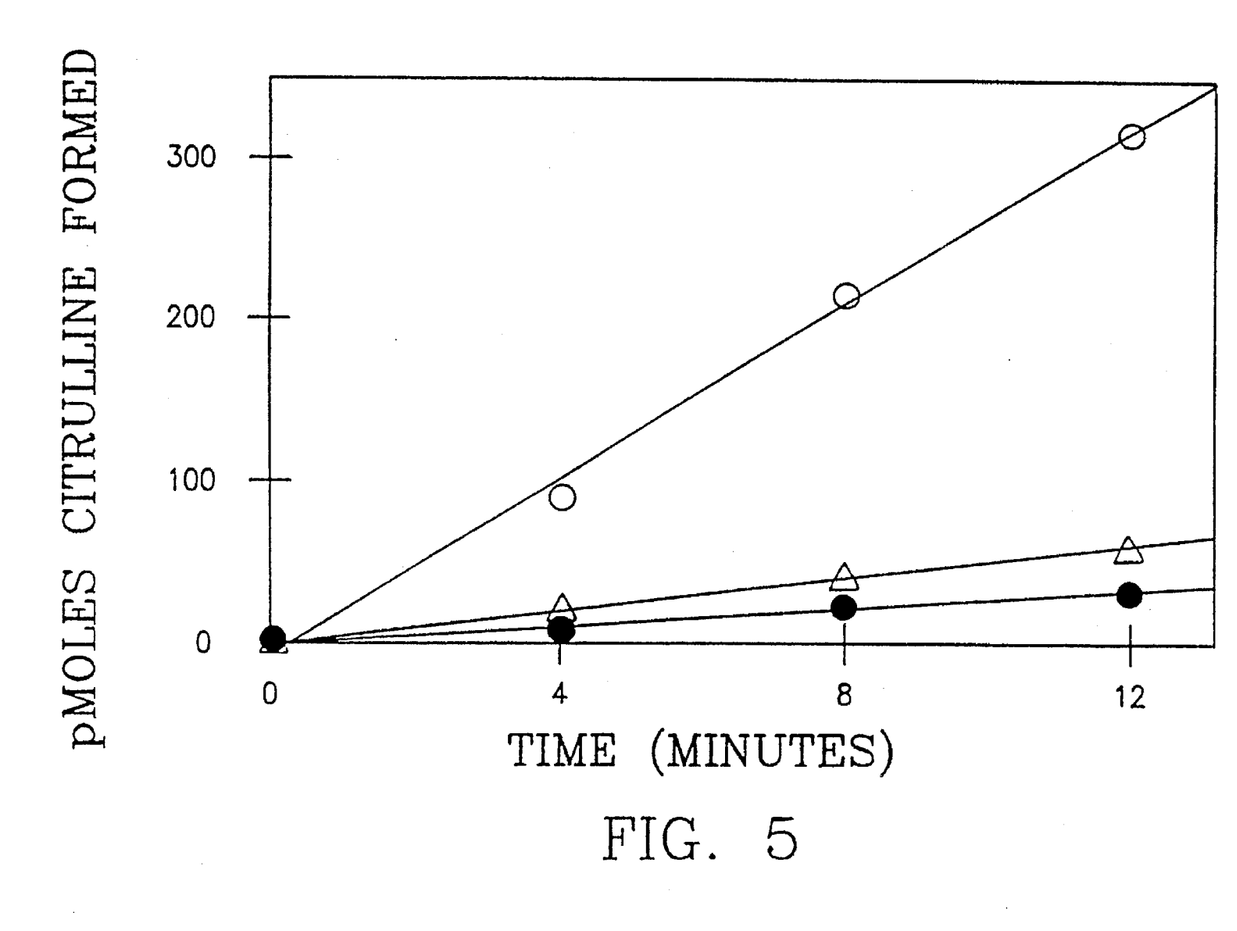
FIG. 5 is a graph of product formation versus time depicting results of Example XI in respect to smooth muscle nitric oxide synthase.

Inhibition of Brain and Smooth Muscle Nitric Oxide Synthase by N$^δ$(2-thienyl)methylimino-L-ornithine and Other Compound The activity of N$^δ$-(2-thienylmethylimino-L-ornithine as an inhibitor of both the constitutive rat brain nitric oxide synthase and the inducible smooth muscle nitric oxide synthase was tested using the protocols previously described in Examples X and VI, respectively. The results are shown in FIG. 4 and FIG. 5 respectively. In both these figures, the line denoted by open circles is the control (20 μM arginine), the line denoted by filled in circles is for 100 μM N$^G$-methyl-L-arginine (L-NMA) and the line denoted by open triangles is for 100 μM N$^δ$-(2-thienyl)methylimino-L-ornithine. As shown in FIG. 4 for the study with brain nitric oxide synthase, citrulline was formed at a constant rate in the presence of 20 μM L-arginine and the absence of inhibitors (control line, open circles). When the reaction mixtures also contain 100 μM N$^δ$-(2-thienyl)methylimino-L-ornithine (open triangles), the rate of citrulline formation was decreased very substantially. For comparison, the extent of inhibition effected by 100 μM L-NMA, the prototypic nitric oxide synthase inhibitor, is also shown (solid circles). Although L-NMA is a somewhat more effective inhibitor than N$^δ$-(2-thienyl)methylimino-L-ornithine, both compounds are extremely effective inhibitors and can be expected to be useful drugs. FIG. 5 shows similar studies with the smooth muscle nitric oxide synthesis (iNOS). As with the rat brain enzyme, N$^δ$-(2-thienyl)methylimino-L-ornithine is an extremely effective inhibitor comparable to, but somewhat less effective than, L-NMA.

EXAMPLE XII

Both common carotid arteries are ligated in two groups of female Sprague-Dawley CFY rats. After 10 minutes, ligations are released and flow is again allowed.

In the case of one group, L-thiocitrulline (20 mg/kg) is administered by bolus injection through a venous catheter 30 minutes after occlusion of the arteries. In the case of the other group, no therapeutic agent is administered.

Histological analysis of stroke volume 24 hours following artery occlusion shows significant reduction in stroke volume for the group administered L-thiocitrulline compared to the group receiving no treatment.

EXAMPLE XIII

Sprague-Dawley rats are injected with 0.25 cc air subdermally in the dorsal area in accordance with an air pouch inflammatory model. The rats in one group are simultaneously administered intraperitoneally L-thiocitrulline (20 mg/kg) and this administration is repeated every 12 hours for 2 weeks. The rats in another group are not administered L-thiocitrulline. At the end of the two-week period the group of rats given L-thiocitrulline have significantly less inflammation than the rats in the other group.

When the same amount of L-homothiocitrulline is substituted for L-thiocitrulline in Examples IV–X, similar results are obtained.

Many variations of the above will be obvious to those skilled in the art. Thus, the invention is defined by the claims.

What is claimed is:

1. Physiologically active arginine or citrulline antagonist compounds including N$^δ$-substituted ornithine or N$^ε$-substituted lysine moieties or monoalkyl carbon-substituted N$^δ$-substituted ornithine or N$^ε$-substituted lysine moieties, having the formula wherein R is $(CH_2)_y CH_3$ or H, R' is $CH_2$ or $C(H)(CH_2)_y CH_3$, and R" is $CH_2$ or $C(H)(CH_2)_y CH_3$, with y ranging from 0 to 5, and x is 0 or 1 and wherein none or only one of R, R' and R" provides an alkyl substituent on ornithine or lysine moiety, and wherein Q is a nitrogen containing heme binding moiety and Q' is —NH$_2$ when there is a double bond between the omega carbon and Q and Q' is =NH when there is a single bond between the omega carbon and Q, and physiologically acceptable acid addition salts thereof.

2. The physiologically active compounds of claim 1 wherein the heme binding moiety constituting Q is a nitrogen-containing heme binding moiety.